United States Patent [19]
Romkee

[11] Patent Number: 5,603,730
[45] Date of Patent: Feb. 18, 1997

[54] SUTURE SLEEVE FOR IMPLANTABLE LEAD

[75] Inventor: D. Scott Romkee, Santa Clara, Calif.

[73] Assignee: Ventritex, Inc., Sunnyvale, Calif.

[21] Appl. No.: 504,281

[22] Filed: Jul. 19, 1995

[51] Int. Cl.$^6$ .................................................. A61N 1/00
[52] U.S. Cl. ........................... 607/116; 606/151; 604/175; 607/115
[58] Field of Search .................................. 606/148, 151, 606/232; 607/115, 116, 119; 604/175

[56] References Cited

U.S. PATENT DOCUMENTS

| | | | |
|---|---|---|---|
| 4,516,584 | 5/1985 | Garcia | 607/119 |
| 5,129,405 | 7/1992 | Milijasevic et al. | 607/116 |
| 5,152,298 | 10/1992 | Kreyenhagen et al. | 607/116 |
| 5,376,108 | 12/1994 | Collins et al. | 607/115 |

*Primary Examiner*—Michael Powell Buiz
*Assistant Examiner*—Mark S. Leonardo
*Attorney, Agent, or Firm*—Steven M. Mitchell; M. Elizabeth Bush; Mark J. Meltzer

[57] ABSTRACT

A suture sleeve having an elongated body defining a bore and having a relief aperture at a first intermediate position on the body and communicating with the bore. The sleeve includes a pair of actuator tabs connected to a second intermediate position on the body and extending therefrom, and at least a portion of the relief aperture is positioned between the tabs such that actuation of the tabs causes enlargement of the aperture. The sleeve may be movable between a tighter state in which a lead passing through the bore does not readily slide longitudinally within the bore, and a looser state, in which the lead may slide readily through the bore.

23 Claims, 3 Drawing Sheets

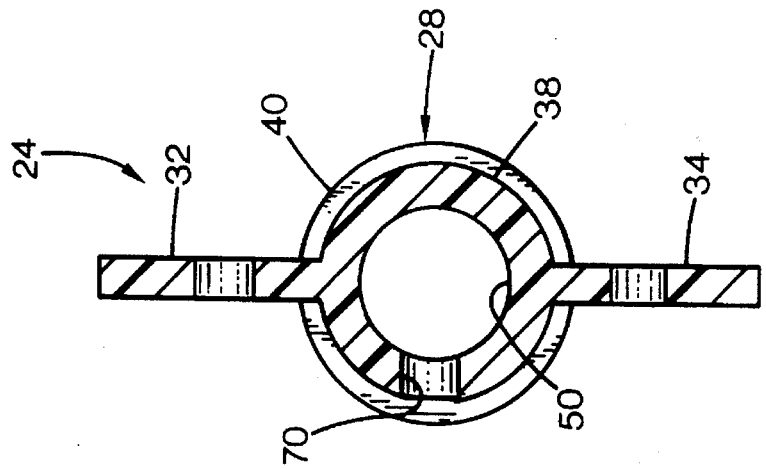
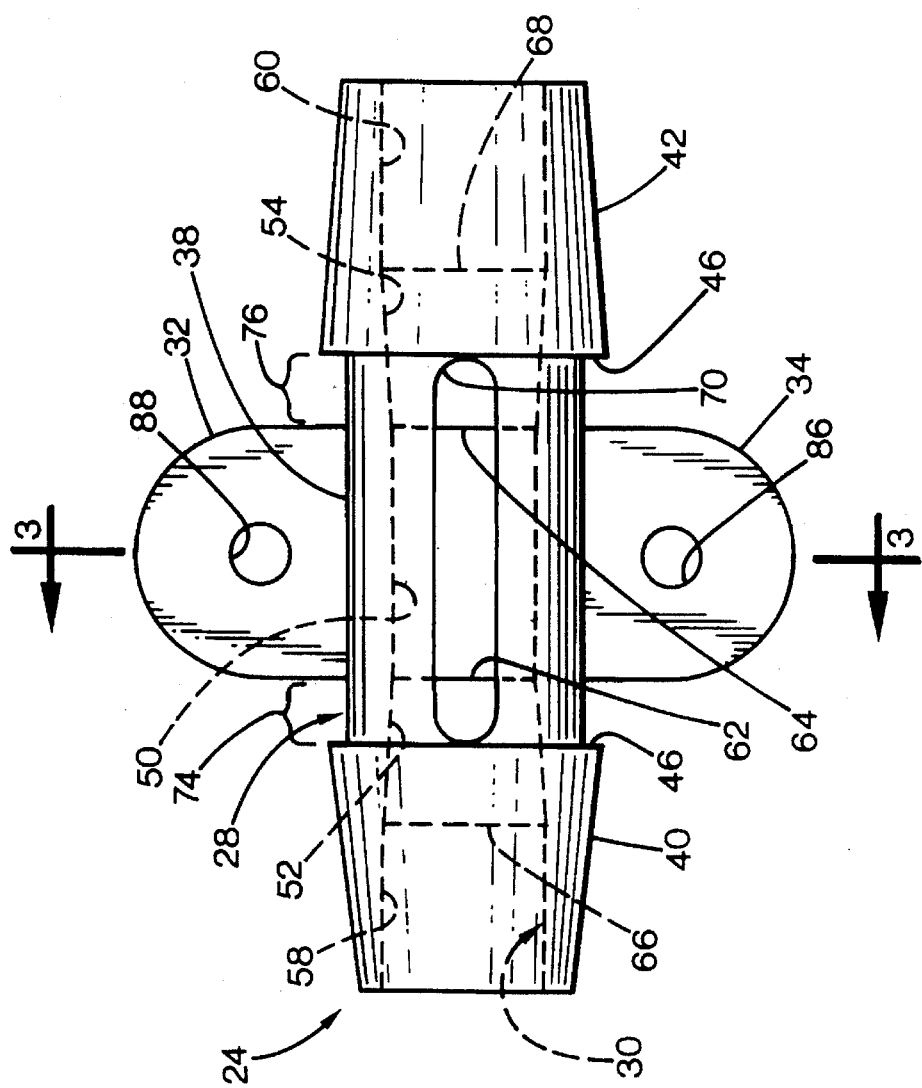
FIG. 3
FIG. 2

SUTURE SLEEVE FOR IMPLANTABLE LEAD

FIELD OF THE INVENTION

The present invention relates generally to implantable medical devices, and more particularly to such devices having elongated leads extending within a patient's body.

BACKGROUND AND SUMMARY OF THE INVENTION

Defibrillators are implanted in patients susceptible to cardiac tachyarrhythmias including tachycardia or fibrillation. Such devices provide cardioversion or defibrillation by delivering a high voltage shock to the patient's heart, typically about 500–750 V. Current devices typically apply this voltage between two transvenously placed electrodes: one at the distal end of a lead inserted into the patient's right ventricle (RV), and the other in the superior vena cava (SVC) region. The lead normally extends from a pectorally or abdominally implanted defibrillator unit, through an incision in the patient's subclavian vein, and to the heart via the vein.

It is important to avoid movement of the lead after it is implanted in the proper position. Shifting of the electrode may also dangerously impair the efficacy of defibrillation shocks from the device by changing the locations across which the voltage is applied. In existing systems, a suture sleeve or collar may be included on the lead. The sleeve may be slid to a selected position on the lead, fixed to the lead in that position, and sutured to the vein or other adjacent tissue. Existing suture sleeves suffer a trade off between the desired attributes of low-resistance positioning and a snug and secure fit when properly positioned. A too tight sleeve will resist sliding along the lead during implantation, risking dislodging of the lead electrodes caused by unwanted motion of the lead. A too loose sleeve may allow the slippage that it was intended to prevent.

The preferred embodiment of the invention overcomes these limitations of the prior art by providing a suture sleeve having an elongated body defining a bore and having a relief aperture at a first intermediate position on the body and communicating with the bore. The sleeve includes a pair of actuator tabs connected to a second intermediate position on the body and extending therefrom, and at least a portion of the relief aperture is positioned between the tabs such that actuation of the tabs causes enlargement of the aperture.

BRIEF DESCRIPTION OF THE DRAWINGS

FIG. 2 is a top view of the embodiment of FIG. 1 in a released position.

FIG. 3 is a sectional end view of the embodiment of FIG. 1 taken along line 3—3.

DETAILED DESCRIPTION OF A PREFERRED EMBODIMENT

Figure 1:
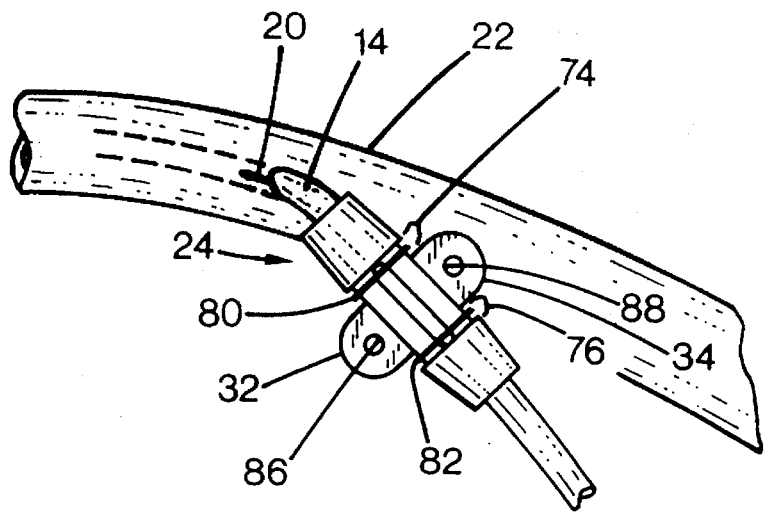
FIG. 1 is an overview of a preferred embodiment of the invention as implanted in a patient.

FIG. 1 illustrates a transvenous lead 14 that is implanted in a patient. The lead 14 of the preferred embodiment is a defibrillation lead or a pacing/sensing lead The lead extends from an implanted defibrillator or pacemaker to the patient's heart, passing through an incision 20 in the patient's subclavian vein 22. A suture sleeve 24 according to the present invention is positioned on the lead 14 at a location near the incision 20, and is secured to adjacent tissue to prevent the lead from being dislodged.

As shown in FIG. 2, the suture sleeve 24 has an elongated tube shaped body 28 defining a central elongated bore 30. A pair of tabs 32, 34 extend laterally from the body. In the preferred embodiment, the body has an overall length of 18 mm, and an exterior profile divided into three segments: a cylindrical central segment 38, and tapered end segments 40, 42. The central segment has a diameter of 4.5 mm. The widest end of each end segment adjoins the central segment. This end of each end segment has a diameter of 5.6 mm, and tapers to a diameter of 3.8 mm at its free end. The difference between the diameter of the central segment and the diameter of the adjacent portion of the end segment forms a shoulder 46 that prevents a suture tied about the central segment from sliding off the end of the body.

The bore 30 has a diameter that changes through the length of the body. A narrowest cylindrical central portion 50 having a diameter of 2.9 mm and a length of 5 mm extends less than the length of the exterior central segment 38. Expanding conical tapered portions 52, 54 adjoin the central portion, and have diameters that match the central portion at their inner ends, and have larger diameters of 3.3 mm at their outer ends. The bore includes cylindrical end portions 58, 60 having diameters matching the outer ends of the tapered portions, and extending by an length of 3.5 mm to the ends of the body. Junction lines 62, 64 define the transition between the central portion 50 and the tapered portions 52, 54. Junction lines 66, 68 define the transition between the tapered portions 52, 54 and the end portions 58, 60. The bore has a smooth and continuous inner surface that is free of bumps and ridges.

The body 28 defines an oblong aperture 70 aligned with the axis of the body, and penetrating the wall of the central segment 38 to provide another opening to the bore. The aperture 70 is a slot extending the entire length of the central segment 38 between the shoulders 46, and has a width of 1 mm, which is less than the smallest diameter of the bore. Aperture 70 may extend past narrowest cylindrical central portion 50 and into expanding conical tapered portions 52, 54, but stopping short of the ends of the suture sleeve body 28.

As best shown in FIG. 3, the tabs 32, 34 extend in opposite directions from each other. The tabs occupy a common plane that passes through the central axis of the body. The tabs are each joined to the body at positions offset by 90 degrees from the aperture 70, and on opposite sides of the aperture. The tabs have a thickness of 1 mm, extend away from the body by a length of 7 mm, and have a width of 5 mm. As shown in FIG. 2, the tabs are centered on the central segment 38, and their narrower widths relative to the length of segment 38 defines a pair of suture grooves 74, 76 around segment 38 between each shoulder 46 and the tabs. Each tab 32, 34 defines a respective hole 86, 88, which may serve for anchoring the sleeve with sutures.

Figure 4:
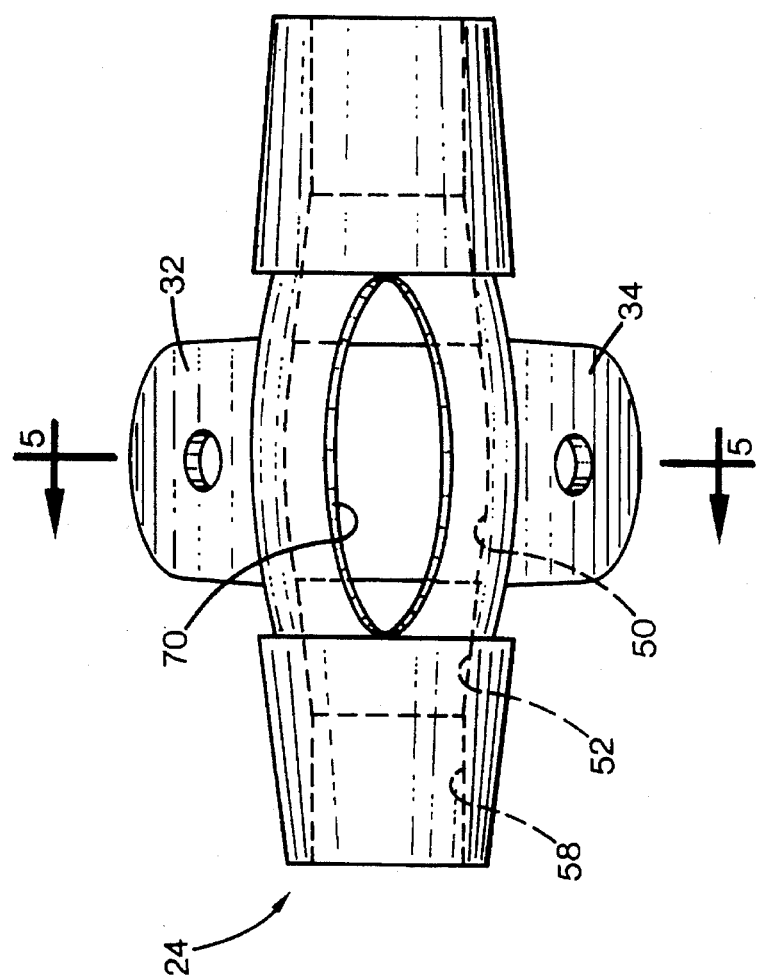
FIG. 4 is a top view of the embodiment of FIG. 1 in an actuated position.

The suture sleeve is an integral unit formed of a resilient elastomer such as polyurethane. In an alternative embodiment, the sleeve may be formed of a composite of elastomer and a semi rigid leaf spring molded into the elastomeric center segment 38. By bending the tabs 32, 34 relative to each other, the sleeve is moved from the unactuated or tighter position shown in FIGS. 2 and 3, to an actuated or looser position shown in FIGS. 4 and 5. In the looser position, the effective diameter of the central portion of the bore is substantially increased to a diameter greater than that of the end portions 58, 60. The aperture 70 gapes open as the tabs are bent or actuated, and the diameter of the center portion of the bore, formerly the smallest diameter portion, is now the largest diameter portion; insertion and sliding of the lead is limited only by the diameter of the end portions of the bore.

To facilitate insertion of the lead 14 into the bore, or to facilitate repositioning of a lead already within the bore, the sleeve is manually moved from the tighter position to the looser position. The lead has a diameter of 3.2 mm, which is smaller than the diameter of the end portions 58, 60 of the bore, yet larger than the diameter of central portion when in the tighter position. Thus, the sleeve in the actuated or looser position has sufficient clearance to slide along the lead without resistance. When the tabs are released to the tighter position, the central portion of the bore grips the lead, preventing the sleeve from sliding readily along the lead. In fact, the sleeve does not entirely return to the original tighter position when a lead is inserted due to the interference fit between the bore and the lead.

Figure 5:
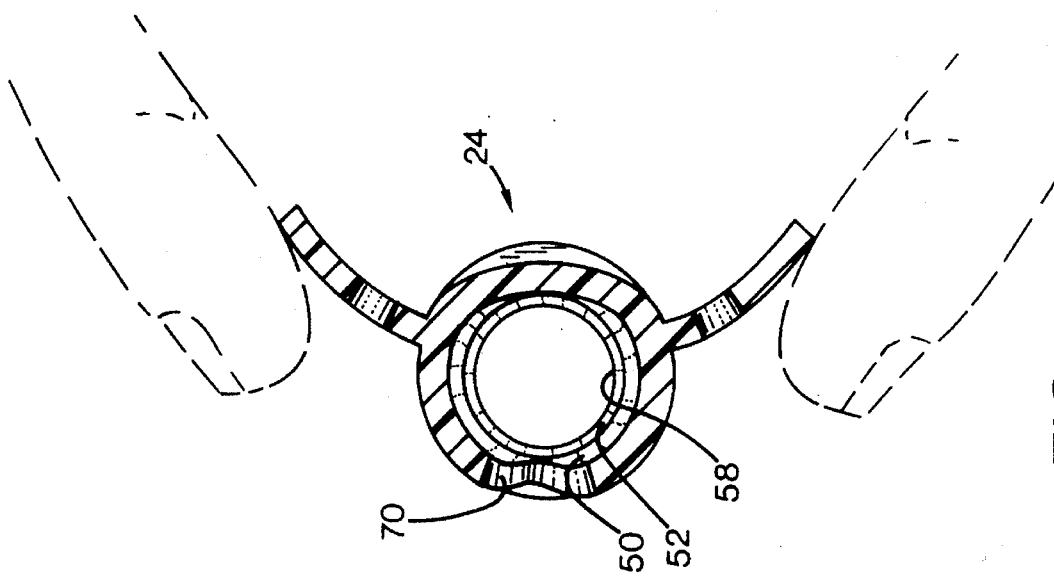
FIG. 5 is a sectional end view of the actuated suture sleeve taken along line 4—4.

As shown in FIG. 5, the tabs may be actuated manually by being bent between the surgeon's fingers. Alternatively, the tabs may be actuated by forceps or any other similar instrument.

In preferred practice, the sleeve is actuated to the looser position, inserted onto the lead, released to the tighter position, and the lead is implanted. After the lead is properly implanted, the sleeve may be actuated, repositioned near the vein incision, and released. The sleeve is then secured to adjacent tissue to anchor it in place. Referring again to FIG. 1, the securement is made by looping sutures 80, 82 about the body at each of the grooves 74, 76, and tying the sutures through adjacent tissue or the vein 22. By tying the sutures to encircle the body at the grooves, the gaping aperture 70 is narrowed, and the body is cinched tightly to the lead.

However, even without the effect of the sutures, the sleeve is biased to the released position to grip the lead. Thus, the surgeon may secure the sleeve to tissue with gently tied sutures to avoid damaging the anchoring tissue. Alternatively, the sutures may be tied through holes 86, 88 in the tabs 32, 34.

While the above disclosure is described in terms of a preferred embodiment, the invention is not intended to be so limited.

I claim:

1. A suture sleeve comprising:

an elongated body having opposed ends and defining a bore extending from end to end of the body;

the body defining an aperture at a first intermediate position on the body and communicating with the bore and spaced from said opposed ends;

a pair of actuator tabs connected to a second intermediate position on the body and extending therefrom; and at least a portion of the aperture being positioned between the tabs such that actuation of the tabs causes enlargement of the aperture.

2. The sleeve of claim 1 wherein the body is movable between a tighter position and a looser position, the bore having a first diameter at the first intermediate position when the sleeve is in the tighter position and the sleeve having a larger second diameter at the first intermediate position when the sleeve is in the looser position.

3. The sleeve of claim 2 wherein the body is biased toward the tighter position.

4. The sleeve of claim 2 wherein each tab has a free end, and wherein the distance between the free ends is greater when the body is in the looser position than when in the tighter position.

5. The sleeve of claim 1 wherein the bore has a limited neck portion having a smaller diameter at the first intermediate position than at the ends of the bore.

6. The sleeve of claim 5 wherein the aperture extends beyond the neck portion toward each end of the body.

7. The sleeve of claim 1 wherein the body defines a pair of circumferential grooves.

8. The sleeve of claim 7 wherein each of the grooves is registered with at least a portion of the aperture, such that sutures tied about the body in the grooves will tend to bias the aperture closed to secure the sleeve to a lead received in the bore.

9. The sleeve of claim 1 formed of a resilient elastomer.

10. The sleeve of claim 1 wherein the tabs extend in substantially opposite directions.

11. The sleeve of claim 1 wherein the tabs are positioned on opposite sides of the body.

12. The sleeve of claim 1 wherein the aperture defines an elongated slot oriented parallel to the length of the body.

13. A method of using a suture sleeve having an elongated body with a bore therethrough, opposed ends, and an aperture spaced from said opposed ends and communicating with said bore, comprising the steps:

inserting an elongated lead through the bore;

moving the body to a looser position;

with the body in the looser position, sliding the sleeve along the lead to a selected position; and moving the body to a tighter position.

14. An implantable lead assembly comprising:

an elongated flexible lead;

a suture sleeve having an elongated body having opposed ends and defining a bore extending from end to end and receiving a portion of the lead;

the body defining an aperture at a first intermediate position on the body and communicating with the bore and spaced from said opposed ends; and a pair of actuator tabs connected to a second intermediate position on the body and extending therefrom such that actuation of the tabs causes enlargement of the aperture.

15. The assembly of claim 14 wherein the body is movable between a tighter position and a looser position, the bore having a first diameter at the first intermediate location when the sleeve is in the tighter position and the sleeve having a larger second diameter at the first intermediate location when the sleeve is in the looser position.

16. The assembly of claim 15 wherein the lead has an outer diameter between the first diameter and the second diameter of the bore.

17. The sleeve of claim 14 wherein the bore has a limited neck portion having a smaller neck diameter at the first intermediate position and a larger end diameter at the ends of the bore.

18. The sleeve of claim 17 wherein the lead has an outer diameter larger than the neck diameter of the bore, and smaller than the end diameter of the bore.

19. A method of securing an implanted lead comprising the steps:

providing an elongated flexible lead having a sleeve defining a bore positioned about said lead;

actuating the sleeve to enlarge the diameter of the bore by spreading open an elongated slot defined in the sleeve and positioned spaced from opposed ends of the sleeve;

while actuating the sleeve, sliding the sleeve along the lead to a selected position; and after sliding the sleeve, releasing the sleeve to reduce the diameter of the bore.

20. The method of claim 19 wherein the step of actuating the sleeve includes actuating elements on the sleeve to enlarge the bore to a diameter greater than the diameter of the sleeve to provide clearance between the lead and the bore.

21. The method of claim 19 wherein the step of spreading open a slot includes actuating a pair of tabs extending from the sleeve adjacent to the slot.

22. The method of claim 19 including the step of tying a ligature about the sleeve at a position encompassing a portion of the slot to prevent spreading of the slot.

23. The method of claim 19 including the step of securing the sleeve to adjacent tissue to immobilize a portion of the lead.

* * * * *